United States Patent [19]
Hofeditz

[11] Patent Number: 4,565,646
[45] Date of Patent: Jan. 21, 1986

[54] WOOL WAX ACID HYDROGENATION PRODUCTS USEFUL AS EMULSIFIERS

[75] Inventor: Wolfgang Hofeditz, Hamburg, Fed. Rep. of Germany

[73] Assignee: Beiersdorf Aktiengesellschaft, Fed. Rep. of Germany

[21] Appl. No.: 584,638

[22] Filed: Feb. 29, 1984

Related U.S. Application Data

[63] Continuation-in-part of Ser. No. 404,770, Aug. 3, 1982, abandoned, which is a continuation of Ser. No. 189,391, Sep. 19, 1982, abandoned.

[30] Foreign Application Priority Data

Sep. 25, 1979 [DE] Fed. Rep. of Germany ....... 2938656

[51] Int. Cl.$^4$ .............................................. B01J 13/00
[52] U.S. Cl. ................... 252/309; 568/885; 568/913; 260/418; 260/428
[58] Field of Search ................ 252/309; 568/885, 913; 260/412.8, 417, 418, 425, 426, 423, 428, 397.25

[56] References Cited

U.S. PATENT DOCUMENTS

| | | | |
|---|---|---|---|
| 2,646,394 | 7/1953 | Green | 568/885 |
| 2,750,429 | 6/1956 | De Nora et al. | 568/885 |
| 3,526,669 | 9/1970 | Fukawa et al. | 568/923 |
| 3,821,121 | 6/1974 | Julian | 252/309 |
| 4,013,731 | 3/1977 | Asahina et al. | 568/923 |
| 4,091,035 | 5/1978 | Clark | 568/913 |

FOREIGN PATENT DOCUMENTS

| | | |
|---|---|---|
| 110505 | 9/1976 | Japan . |
| 355484 | 8/1931 | United Kingdom . |
| 961337 | 6/1964 | United Kingdom . |
| 660969 | 5/1979 | U.S.S.R. . |

OTHER PUBLICATIONS

Stickdorn et al., *Tenside*, 3, 1966, p. 48, (summary).
Truter, *Wool Wax*, Cleaver-Hume Press Ltd., London, 1956, p. X.
Hackh's Chemical Dictionary, 4th ed. McGraw-Hill Book Co., N.Y., (1969), p. 98.

*Primary Examiner*—John F. Terapane
*Assistant Examiner*—Anne Brookes
*Attorney, Agent, or Firm*—Jordan B. Bierman

[57] ABSTRACT

An emulsifier for oil-in-water emulsions consisting essentially of a substantially steroid-free wool-wax alcohol free of $\alpha,\omega$-diols prepared by subjecting (a) wool-wax esters of mono- or multi-valent alcohols of 1 to 6 carbon atoms or
(b) wool-wax alcohols optionally containing monovalent aliphatic alcohols of 1 to 6 carbon atoms to catalytic hydrogenation at a pressure of 170 to 300 bars and a temperature of 200° to 300° C. in the presence of a high pressure hydrogenation catalyst to obtain substantially steroid-free wool wax alcohols and removing therefrom $\alpha,\omega$-diols useful as emulsifiers.

9 Claims, No Drawings

WOOL WAX ACID HYDROGENATION PRODUCTS USEFUL AS EMULSIFIERS

This application is a continuation-in-part of Ser. No. 404,770, filed Aug. 3, 1982, which is a continuation of Ser. No. 189,391, filed Sept. 19, 1980, which in turn claims the priority of German Application No. P 29 38 656.9, filed Sept. 25, 1979, both now abandoned.

The present invention relates to a method of preparing an emulsion using emulsifiers which are steroid-free wool wax alcohols obtained by high-pressure hydrogenation of wool wax acids or of corresponding acid esters of lower alcohols. The emulsifiers can be used for manufacturing of water-in-oil emulsions.

Wool wax alcohols have been prepared from wool wax by two substantially different processes. The first process comprises the saponification of the wool wax with bases, followed by extraction of the wool wax alcohols with organic solvents. The second process is the high-pressure hydrogenation of wool wax to the corresponding alcohols. In this process, the esters are hydrolyzed, and the acids are transformed into the corresponding alcohols.

A basic disadvantage of the saponification process resides in the fact that the yield of alcohols obtainable by this method is only about 45%, based on the starting material. The remainder comprises a mixture of organic acids (the wool wax acids), and is a rather sticky mass having a wax-like consistency. It is regarded as an undesirable by-product for which no real use has as yet been found, despite great efforts.

On the other hand, the wool wax alcohol fraction obtained by the saponification method furnishes, after separation and refining, a particularly high-grade water-in-oil emulsifier, extremely useful and desirable for cosmetic and pharmaceutical purposes. The alcohol contains steroids such as cholesterol and lanosterol, which occur in the wool wax, in their natural and unchanged form.

The high-pressure hydrogenation process of wool wax is capable of producing high yields of wool wax alcohols (of the order of approximately 90%), based on the starting material. The resultant product also has water-in-oil emulsification properties, but the quality thereof is substantially lower than the product of the saponification process. It is believed that this is attributable both to the hydrogenation of the double bonds and the partial isomerization of the steroids contained in the wool wax. These very steroids are the substances which provide the superior emulsifying properties.

Until the present invention, the wool wax acids obtained as the residue from the saponification process have been essentially regarded as a mere waste product.

Therefore, it is an object of this invention to provide a profitable and commercially satisfactory use for the large proportion of wool wax acids obtained in the saponification of wool wax.

It is also among the objects of this invention to provide a similar profitable and commerical use for the esters of such acids with short-chain aliphatic alcohols or polyols.

It is further object of the present invention to prepare from the wool wax acids, or esters thereof, emulsifiers which are useful for cosmetic and pharmaceutical purposes for the production of water-in-oil emulsions. In passing, it should be noted that there is a great demand for good emulsifiers of this type because of the limited number which are presently known as being useful for this purpose.

The first part of the solution to the foregoing problem resides in the discovery that, when applying the known high-pressure hydrogenation process to wool wax acids or lower alcohol esters thereof, if certain reaction conditions are maintained, the desired alcohols can be obtained in high yield as a white, wax-like product. In view of the complex nature of wool wax acids, such result is unpredicatable. As a matter of fact, the person of ordinary skill would expect that, due to the complex nature of the composition of the wool wax acids, use of the high-pressure hydrogenation would probably cause cracking of the molecules involved.

Under the conditions of the present invention, the steroid-free wool wax alcohols which result from high-pressure hydrogenation of the corresponding wool wax acids or esters thereof, contain essentially straight chain as well as terminal methyl- and ethyl-branched primary alcohols and 1,2-diols having 10 to 32 carbon atoms. In addition, the products contain $\alpha,\omega$ diols which are formed from the corresponding $\omega$-hydroxy carbonic acids or esters by hydrogenation.

When the properties of the foregoing compositions were tested, it was found that such wool wax alcohols have inadequate water-in-oil emulsification properties, especially when compared with the wool wax alcohols resulting from the saponification process. It is believed that the difference is caused by the presence of the aforementioned diols, which have pronounced anti-emulsification properties and which interfere with the emulsification process.

The solution to the foregoing problem, which also constitutes the second portion of the present invention, resides in the removal of the offending diols prior to the use of the wool wax alcohols as emulsifiers. The diols should be removed by either molecular distillation or crystallization. When this is done, the resultant wool wax alcohols are capable of matching the water absorption capacity of wool wax alcohols obtained by the saponification process. In addition, they are not inferior to the saponification alcohols in their water-in-oil emulsification properties.

The subject matter of the present invention is a method for the production of emulsifier utilizing wool wax alcohols obtained by high-pressure hydrogenation, wherein the starting materials are (1) wool wax acids in the presence or absence of monovalent aliphatic alcohols having 1 to 6 carbon atoms, or (2) wool wax acid esters of lower alcohols. These materials are subjected to high-pressure hydrogenation, in the presence of a customary catalyst therefore, at a pressure of 170 to 300 bar and a temperature of 200° to 300° C., preferably 250° to 280° C. The steroid-free alcohols obtained in this manner are subsequently subjected to either molecular distillation or crystallization. Either of these two processes separates the $\alpha,\omega$ diols which interfere with the emulsification properties.

The preferred hydrogenation catalyst is copper chromite. While it has been found preferable to carry out the hydrogenation under a pressure of 220 to 240 bar and a temperature of 250° to 280° C., it is also advantageous to hydrogenate at 260 to 280 bar at a temperature of 250° to 270° C. The term "lower alcohols" includes both monovalent and multivalent aliphatic alcohols having 1 to 6 carbon atoms. For example, methyl, ethyl, isopropyl, and glycerol esters are all quite suitable. In addition, the wool wax acid ester of pentaerythritol is also desirable.

Anhydrous methanol or absolute ethanol are examples of suitable monovalent, lower aliphatic alcohols which may be used as diluents for the wool wax acids in the present process.

The molecular distillation used to remove the unwanted diols is carried out under the usual conditions. The crystallization step, which is an alternative to molecular distillation, is readily carried out by dissolving the diol-containing reaction product in gasoline. The diols will separate in the cold as a white precipitate.

The process of the present invention opens new possibilities for use of the wool wax acids which are obtained in large quantities as a waste product from the saponification of wool wax. The esters obtainable therefrom by reaction with short-chain alcohols or polyols can also be used for hydrogenation. Once the undesired diols have been removed from these hydrogenated materials, the resulting products are particularly useful as emulsifiers for the production of water-in-oil emulsions for use in the cosmetic or pharmaceutical industries. They can be used alone or blended with wool wax alcohols produced by saponification of wool wax and/or other known water-in-oil emulsifiers. In addition, they are suitable as part of the oil phase, consistency providers, and/or auxiliary emulsifiers in both water-in-oil and oil-in-water emulsions in place of fatty alcohols currently being used.

As a result of the present invention, the known saponification process can be supplmented by high-pressure hydrogenation of the hitherto waste product wool wax acids followed by purification by molecular distillation or crystallization. This yields two high-grade water-in-oil emulsifiers. The wool wax used can similarly be converted almost quantitatively into wool wax alcohols. It is necessary to go through two stages, but it is important to note that both a steroid-containing and a steroid-free wool wax alcohol fraction are obtained. These are of approximately the same quality as the saponification alcohols insofar as emulsification properties are concerned. Of course, the steroid-containing fraction contains the natural steroids, unaffected by hydrogenation, which occur in the wool wax.

A particularly preferred form of the present invention provides for substitution of up to 25% by weight, preferably 5-10%, of the wool wax alcohol, with a steroid such as cholesterol, lanosterol, sitosterol, campesterol, stigmasterol or mixtures thereof to the steroid-free wool wax alcohols resulting from high-pressure hydrogenation. However, if molecular distillation is to be carried out, the addition must be made prior to that step. On the other hand, if the unwanted diols are separated by crystallization, the steroids must be added subsequent to the separation.

A further advantage of the preferred form of this invention resides in the fact that cheap plant steroids such as sitosterol, campesterol, stigmasterol, or mixtures thereof, may be used in place of the substantially more expensive cholesterol and lanosterol. Since the plant steroids can be obtained from soy oil or tall oil, it is now possible to obtain non-ionogenic emulsifiers economically. Moreover, the properties of such emulsifiers are equivalent to the steroid-containing wool wax alcohols obtained by the saponification of wool wax.

The wool wax aids, which are the starting product for the method of the present invention, are readily obtained by saponifying wool wax by the usual methods. After separation of the wool wax alcohols by extraction with an organic solvent, the metal soaps are acidified, whereby the free acids (wool wax acids), are obtained. These crude acids are subjected to molecular distillation for purification and separation of substances which might act as catalyst poisons. The distilled acids or esters produced therefrom by reaction with short-chain alcohols or polyols are then subjected to high-pressure hydrogenation under the above-described conditions.

The following examples are intended to illustrate the present invention.

EXAMPLE 1

500 grams of distilled wool wax acids are charged, together with 80 ml absolute ethanol and 25 grams of copper chromite into a 2 liter autoclave. The apparatus is first flushed with nitrogen, and then hydrogen is forced into the device under a pressure of 160 to 170 bar. The reactor is heated to 260° to 270° C. As a result, the pressure increases to 260 to 280 bar, and then drops to a constant value of 230 to 240 bar over the course of 4 hours. After cooling, the reaction mixture is removed from the autoclave and the catalyst is filtered off. A white mass having a waxy consistency at room temperature and a pleasant odor is obtained. This mass is subsequently subjected to further purification and separation of the $\alpha,\omega$ diols either molecular distillation under the usual conditions or crystallization from gasoline. The unwanted diols separate in the cold as a white precipitate therefrom.

EXAMPLE 2

Instead of the wool wax acids, 500 grams of the corresponding methyl or ethyl esters thereof are charged into the autoclave. No absolute ethanol is necessary. The reaction is otherwise carried out as described in Example 1. The parameters determined from several batches of wool wax alcohols thus produced are as follows:

Acid number: max.0.6
Saponification No.: 2 to 7
Hydroxyl No.: 210 to 250

In order to demonstrate the good emulsification properties of wool wax alcohols obtained according to the present invention, comparative tests were carried out with other, similarly produced emulsifiers. The results have been compiled in Table I. The emulsifying number of the individual emulsifiers was determined in accordance with the following method:

1.0 grams of the emulsifier to be tested were dissolved hot in 19 grams of paraffin oil. 10 grams of this mixture were introduced into a vessel having an agitator and the temperature thereof was maintained at 50° C. The mixture was stirred with a mixing whip at 150 revolutions per minute. At equal intervals of time, 5 ml of water at 50° C. were added to the mixture contained in the agitator vessel. The addition was continued until the emulsion formed no longer absorbed water, as is recognized by drop formation and slipping of the emulsion. During the addition of water, the vessel was covered with plastic panels to prevent evaportion. The emulsifying number, which equals the ml of water consumed multiplied by 10, is a measure of the water absorption capacity of the emulsifier and indicates how many ml of water can be emulsified into 100 grams of paraffin oil containing 5% emulsifier. It is an indirect measure of the emulsifying capacity of water-in-oil emulsifiers generally. The processes referred to in Table 1 are those designated on page 5.

TABLE I

| Emulsifier | Emulsifying number | Emulsion formation |
|---|---|---|
| Wool wax | 800 | Pseudo emulsion |
| Wool wax acids | 300 | None |
| Wool wax alcohols from saponification (acc. to process 1) purified by distillation | 1900 | Very good |
| Wool wax alcohols obtained by hydrogenation of wool wax (according to process 2) (4 different samples of commercial products of various manufacturers) | x (sample 1) 250 (sample 2) 300 (sample 3) x (sample 4) | None Pseudo emulsion Pseudo emulsion None |
| Wool wax alcohols obtained by hydrogenation of wool wax acids (according to the process of the invention), and then removing the $\alpha,\Omega$-diols therefrom | 1950 | Very good |
| Wool wax alcohols obtained by hydrogenation of wool wax acids (according to the process of the invention), without separation of the $\alpha,\Omega$-diols | 800 | Pseudo emulsion | x = No water take-up

Using the alcohols produced by the process of the present invention, water-in-oil emulsions (creams) were produced in accordance with the following procedure.

| Fat phase | Water phase |
|---|---|
| 30 parts by wt. emulsifier | 5 parts by wt. magnesium sulfate |
| 15 parts by wt. cetyl/stearyl alcohol | 30 parts by wt. glycerol |
| 30 parts by wt. ozokerite | 608 parts by wt. water |
| 20 parts by wt. table paraffin | 643 parts by wt. |
| 20 parts by wt. vaseline | |
| 240 parts by wt. paraffin oil | 2 parts by wt. perfume |
| 355 parts by wt. | |

The water-in-oil emulsion base is comprised of the fat phase, the water phase, and perfume.

The components of the fat phase were melted in an agitator vessel at 80° C. and mixed with the water phase which was heated to 75° to 80° C. while stirring. The stirring continued, and the mixture was permitted to cool. The perfume was added at approximately 35° C. and stirring was continued until the mixture became cold. The cream thus obtained was homogenized in a homogenizer.

The stability of the cream at room temperature, in a refrigerator and heating cabinet (with a temperature range of $-15°$ to $+25°$ C.) in the rocking test, and in an incubator at 53° C., was measured for a period of at least one month. The results are set forth in Table II.

TABLE II

| Water-in-oil emulsion base + 3% emulsifier | |
|---|---|
| Emulsifier: | |
| Wool wax alcohols obtained by hydrogenation of wool wax acids (according to the invention) | soft cream, no emergence of water on rolling 53° test: coalesced somewhat cold stability test: very good. |
| Wool wax alcohols obtained by hydrogenation of wool wax acids (acc. to the invention), 5 and 10% thereof (two samples) was replaced by Biosterol | good cream, no emergence of water on rolling 53° test: not coalesced Cold stability: very good |
| Wool wax alcohols obtained by hydrogenation of wool wax acids (acc. to the invention) blended with wool wax alcohols obtained from saponification of wool wax (acc. to process 1) in ratio 1:1 | firm cream, no water emerges on rolling 53° test: not coalesced Cold stability: only moderate |

Biosterol consists of 42% sitosterol, 25% campesterol and 22% stigmasterol.

The data set forth in Table I indicates that the purified wool wax alcohols obtained by the process of the present invention are excellent water-in-oil emulsifiers and are substantially equivalent to the steroid-containing wax alcohols resulting from the saponification process. In comparison, the total hydrogenation of wool wax, in accordance with the high-pressure hydrogenation process, yields alcohols of only moderate emulsification ability. A further major advantage of the present invention resides in the stablity to aging and hydrolysis, as well as the possibility of influencing the consistency of the emulsion by appropriate addition of steroids. At the same time, this will not appreciably alter the water absorption capacity of the emulsifier. Table III evidences these facts.

As can be seen from the following Table III, it is possible to substantially modify the properties of the emulsions prepared with emulsifiers obtained from the process of the present invention. Throughout wide limits, the water absorption ability is not adversely affected. The same is also true of formulations with wool wax alcohols obtained by saponification of wool wax. Thus, by the addition of steroids, both the strength and the thermal stability of a water-in-oil emulsion can be favorably influenced.

While only a limited number of embodiments of the present invention have been expressly described, it is, nonetheless, to be broadly construed and not to be limited except by the character of the claims appended hereto.

TABLE III

| | Weight-% | | | | | | | | | | | | |
|---|---|---|---|---|---|---|---|---|---|---|---|---|---|
| Wool wax alcohols obtained by hydrogenation of wool wax acids (acc. to the invention), and then removing the $\alpha,\Omega$-diols therefrom | 100 | — | 95 | 90 | 85 | 80 | 95 | 90 | 85 | 80 | 95 | 90 | 85 | 80 |
| Wool wax alcohols obtained by hydrogenation of wool wax acids (acc. to the invention) blended with wool wax alcohols obtained from saponific. of wool wax (acc. to process 1) in ratio 1:1 | — | 100 | — | — | — | — | — | — | — | — | — | — | — | — |
| Cholesterol | — | — | 5 | 10 | 15 | 20 | — | — | — | — | — | — | — | — |
| Lanosterol | — | — | — | — | — | — | 5 | 10 | 15 | 20 | — | — | — | — |

TABLE III-continued

| | Weight-% | | | | | | | | | | | | | |
|---|---|---|---|---|---|---|---|---|---|---|---|---|---|---|
| Mixture of Cholesterol and Lanosterol in ratio 1,5:1 | — | — | — | — | — | — | — | — | — | — | 5 | 10 | 15 | 20 |
| Emulsifying number | 1950 | 1800 | 1925 | 1850 | 1750 | x | 1850 | 1850 | 1450 | 1300 | 1925 | 1775 | 1725 | 1700 |
| Wool wax alcohol obtained by hydrogenation of wool wax acids (acc. to the invention), and then removing the $\alpha,\Omega$-diols therefrom | 100 | 95 | 90 | 85 | 80 | 95 | 90 | 85 | 80 | 95 | 90 | 85 | 80 | |
| Mixture of Cholesterol and Lanosterol in ratio 2:1 | | 5 | 10 | 15 | 20 | — | — | — | — | — | — | — | — | |
| Sitosterol | | — | — | — | — | 5 | 10 | 15 | 20 | — | — | — | — | |
| Biosterol | | — | — | — | — | — | — | — | — | 5 | 10 | 15 | 20 | |
| Emulsifying number | 1950 | 1875 | 1975 | 1725 | x | 1900 | 1900 | 1850 | 1800 | 1850 | 1850 | 1850 | 1750 | | x = no water take-up

I claim:

1. An emulsifier for oil-in-water emulsions consisting essentially of a substantially steroid-free wool-wax alcohol free of α,ω-diols prepared by subjecting
   (a) wool-wax esters of mono- or multivalent alcohols of 1 to 6 carbon atoms or
   (b) wool-wax acids optionally containing monovalent aliphatic alcohols of 1 to 6 carbon atoms to catalytic hydrogenation at a pressure of 170 to 300 bars and a temperature of 200° to 300° C. in the presence of a high pressure hydrogenation catalyst to obtain substantially steroid free wool wax alcohols and removing therefrom α,ω-diols.

2. The emulsifier of claim 1 wherein the hydrogenation temperature is 250° C. to 280° C.

3. The emulsifier of claim 1 wherein the catalyst is copper chromite.

4. The emulsifier of claim 1 wherein up to 25% by weight of the steroid-free wool wax alcohol is replaced by an equal weight of a steroid.

5. The emulsifier of claim 4 wherein 5 to 10% by weight of said wool wax alcohol is replaced by an equal amount of a steroid.

6. The emulsifier of claim 4 wherein said steroid is selected from the group consisting of cholesterol, lanosterol, sitosterol, campesterol, stigmasterol, and mixtures thereof.

7. The emulsifier of claim 1 wherein said diols are crystallized from cold gasoline.

8. The emulsifier of claim 4 wherein said steroid is added to said substantially steroid-free wool-wax alcohols prior to said molecular distillation step or after said crystallization step.

9. An oil-in-water emulsion containing an emulsifying effective amount of an emulsifier of claim 1.

* * * * *